United States Patent
Nakata et al.

(10) Patent No.: US 10,302,659 B2
(45) Date of Patent: May 28, 2019

(54) METHOD FOR EVALUATING THE POSSIBILITY OF SUFFERING FROM PANCREATIC DISEASE

(71) Applicant: OLYMPUS CORPORATION, Hachioji-shi, Tokyo (JP)

(72) Inventors: Mari Nakata, Tokyo (JP); Hiromi Sanuki, Yokohama (JP); Tetsuhide Takeyama, Tokyo (JP); Shoji Tokunaga, Fukutsu (JP); Masao Tanaka, Fukuoka (JP)

(73) Assignee: OLYMPUS CORPORATION, Hachioji-shi (JP)

( * ) Notice: Subject to any disclaimer, the term of this patent is extended or adjusted under 35 U.S.C. 154(b) by 0 days.

(21) Appl. No.: 15/961,012

(22) Filed: Apr. 24, 2018

(65) Prior Publication Data

US 2018/0238906 A1 Aug. 23, 2018

Related U.S. Application Data

(63) Continuation of application No. PCT/JP2016/078449, filed on Sep. 27, 2016.

(30) Foreign Application Priority Data

Oct. 26, 2015 (JP) .................. 2015-209867

(51) Int. Cl.
G01N 33/53 (2006.01)
G01N 33/68 (2006.01)
G01N 33/48 (2006.01)

(52) U.S. Cl.
CPC ......... *G01N 33/6893* (2013.01); *G01N 33/48* (2013.01); *G01N 33/68* (2013.01); *G01N 2333/4727* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 8,529,547 B2* | 9/2013 | Sanuki | G01N 33/57438 604/319 |
| 8,586,384 B2* | 11/2013 | Moriya | A61B 5/14865 436/514 |
| 2014/0030823 A1* | 1/2014 | Sanuki | G01N 33/6893 436/501 |

FOREIGN PATENT DOCUMENTS

| | | |
|---|---|---|
| EP | 2 696 202 A1 | 2/2014 |
| JP | 2006-308576 A | 11/2006 |
| JP | 2012-502285 A | 1/2012 |
| JP | 2014-115188 A | 6/2014 |
| JP | 2015-011011 A | 1/2015 |
| WO | 2010/028658 A1 | 3/2010 |
| WO | 2012/137832 A1 | 10/2012 |

OTHER PUBLICATIONS

Mori et al (Pancreas, 2013, 42(2): 187-192).*
Matsumoto et al. "Evaluation of Cytology and Tumor Markers of Pure Pancreatic Juice for the Diagnosis of Pancreatic Cancer at Early Stages." Pancreas, 1994, vol. 9, pp. 741-747.
Yokoyama et al. "Matrix Metalloproteinase-2 in Pancreatic Juice for Diagnosis of Pancreatic Cancer." Pancreas, 2002, vol. 24, pp. 344-347.
Morita et al. "Ieki Junishichoeki." The Japanese Journal of Clinical and Experimental Medicine, Mar. 1981, vol. 58, pp. 832-838.
Mori et al. "Suigan Screening o Mezashita Teishinshu na Junishichoeki Saishu to Tanpaku Marker no Kaiseki." Gastroenterol Engdosc, Apr. 10, 2012, vol. 54, pp. 1221.
Dec. 27, 2016 International Search Report issued in International Patent Application PCT/JP2016/078449.

* cited by examiner

*Primary Examiner* — Sean E Aeder
(74) *Attorney, Agent, or Firm* — Oliff PLC

(57) ABSTRACT

The purpose of the present invention is to provide a method for evaluating the possibility of suffering from pancreatic disease on the basis of the concentration of a pancreatic disease marker in a duodenal juice sample. The method for evaluating the possibility of suffering from pancreatic disease of the present invention has a step for (a) measuring the concentration of the pancreatic disease marker in a duodenal juice sample taken from a subject and a step for (b) evaluating the possibility of the subject suffering from pancreatic disease on the basis of the concentration of the pancreatic disease marker measured in step (a) and the age of the subject.

1 Claim, 3 Drawing Sheets

METHOD FOR EVALUATING THE POSSIBILITY OF SUFFERING FROM PANCREATIC DISEASE

CROSS REFERENCE TO RELATED APPLICATIONS

This application is a continuation application according to a PCT Patent Application No. PCT/JP2016/078449, filed on Sep. 27, 2016, whose priority is claimed on Japanese Patent Application No. 2015-209867, filed Oct. 26, 2015, the entire contents of which are hereby incorporated by reference.

BACKGROUND OF THE INVENTION

Field of the Invention

The present invention relates to a method for evaluating the possibility that a subject suffers from a pancreatic disease according to the concentration of a pancreatic disease marker in a duodenal juice sample.

Description of the Related Art

A method of determining the presence or absence of various diseases such as cancer by using the concentration of biomolecules in the body fluid of the subject as an indicator has been widely performed. For example, Japanese Unexamined Patent Application, First Publication No. 2014-115188 discloses a method of detecting a cancer of a subject using the amount of CSRP1 protein or the presence or absence of CSRP1 protein in the blood of a subject as an index. In addition, Japanese Unexamined Patent Application, First Publication No. 2012-502285 discloses a method of comparing YKL-40 concentration in a body fluid such as the blood with a cutoff value adjusted for age, so as to determine the presence or absence of gastrointestinal cancer or the severity thereof, select a treatment method thereof, or the like.

The duodenal juice is a mixed fluid of the pancreatic juice discharged from the pancreas, the bile discharged from the bile duct, and the mucus secreted by the duodenum. The duodenal juice can be collected by simply inserting an endoscope to the duodenum to aspirate the duodenal juice at that place, which can be performed with less invasive and simpler procedures than sampling of the pancreatic juice from the pancreatic duct. Therefore, pancreatic diseases can be examined by detecting the pancreatic disease marker in the duodenal juice (see, for example, Japanese Unexamined Patent Application, First Publication No. 2015-11011).

SUMMARY

An aspect of the present invention is a method of evaluating a possibility of suffering from pancreatic cancer, including: (a) measuring a concentration of a pancreatic disease marker in a duodenal juice sample collected from a subject; and (b) evaluating the possibility of suffering from pancreatic cancer of the subject by comparing a score value, which is obtained by correcting a decrease due to age with respect to the concentration of the pancreatic disease marker measured in the step (a) in accordance with an age of the subject, with a cutoff value, wherein the pancreatic disease marker is S100P protein.

An aspect of the present invention is a method of evaluating a possibility of suffering from pancreatic cancer, including: (a) measuring a concentration of a pancreatic disease marker in a duodenal juice sample collected from a subject; and (b) evaluating the possibility of suffering from pancreatic cancer of the subject by comparing the concentration of the pancreatic disease marker measured in the step (a) with a cutoff value obtained by correcting a decrease due to age with respect to the concentration of the pancreatic disease marker in accordance with the age of the subject, wherein the pancreatic disease marker is S100P protein.

In the step (b), a score value may be calculated by correcting a decrease due to age with respect to the concentration of the pancreatic disease marker measured in the step (a) in accordance with the age of the subject, and when the score value is equal to or higher than a cutoff value set uniformly regardless of the age of the subject, it may be determined that there is a high possibility that the subject is developing pancreatic cancer, and when the score value is less than the cutoff value, it may be determined that there is a low possibility that the subject is developing pancreatic cancer.

In the step (b), when the concentration of the pancreatic disease marker is equal to or higher than a cutoff value obtained by correcting a decrease due to age with respect to the concentration of the pancreatic disease marker in accordance with the age of the subject, it may be determined that there is a high possibility that the subject is developing pancreatic cancer, and when the concentration of the pancreatic disease marker is less than the cutoff value, it may be determined that there is a low possibility that the subject is developing pancreatic cancer.

The cutoff value obtained by correcting a decrease due to age with respect to the concentration of the pancreatic disease marker may be corrected to be lower as the age of the age group becomes higher.

DETAILED DESCRIPTION OF THE PREFERRED EMBODIMENTS

Figure 1:
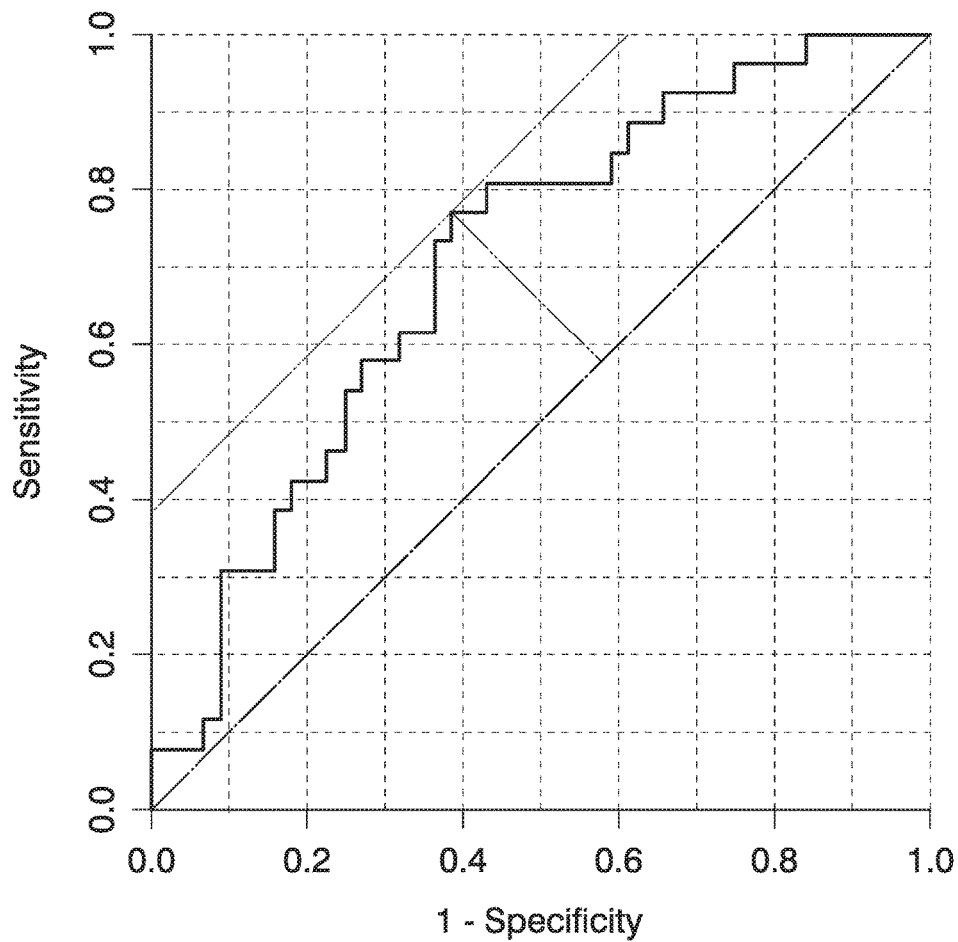
FIG. 1 is an ROC curve created from common logarithmic values of S100P concentration in each subject in Example 1.

In the present invention and the specification of the present application, the pancreatic disease marker is various biomolecules such as proteins, nucleic acids, lipids, cells and the like contained in the pancreatic juice, and their concentration in the pancreatic juice is significantly higher in a pancreas-diseased subject, compared with that in a pancreatic disease-unaffected subject. Incidentally, pancreatic disease-unaffected subjects are those whose pancreas is normal and not limited to healthy individuals, but also those suffering from diseases other than pancreatic diseases. Examples of the pancreatic diseases are, for example, the pancreatic cancer, the IPMN (intraductal papillary mucinous neoplasm), the MCN (mucinous cystic neoplasm), the SCN (serous cystic neoplasm), the NET (pancreatic neuroendocrine tumor), the chronic pancreatitis (CP), the acute pancreatitis, and the like.

In the present invention and in the specification of the present application, the cutoff value means a value used to distinguish the target group of pancreas-diseased subjects from the group of pancreatic disease-unaffected subjects, as for the concentration of the pancreatic disease marker or a value derived from the concentration. The cutoff value to distinguish the group of pancreas-diseased subject from the group of pancreatic disease-unaffected subject can be set experimentally in consideration of the type of the pancreatic disease marker, the method of measuring the concentration of the pancreatic disease marker, and the like. As an example of a method of setting the cutoff value, for example, first, the concentration of the pancreatic disease marker is measured respectively, as for the duodenal juice collected from a sufficient number of subjects who are known not to be suffering from pancreatic disease and the duodenal juice collected from a sufficient number of subjects who are known to be suffering from pancreatic disease. Next, an ROC curve (Receiver Operating Characteristic Curve) is created for the measured value or the score value derived from the measured value. According to this ROC curve, it is possible to set the cutoff value so that the desired sensitivity and specificity are obtained.

In order to evaluate the possibility of suffering from pancreatic disease, it is preferable to set the cutoff value so that the specificity is 80% or more, it is more preferable to set the cutoff value so that the specificity is 85% or more, and it is further preferable to set the cutoff value so that the specificity is 90% or more.

The method for evaluating the possibility of suffering from pancreatic disease according to the present invention (hereinafter sometimes referred to as "the evaluation method according to the present invention") is a method for evaluating the possibility of suffering from pancreatic disease using the concentration of the pancreatic disease marker in the duodenal juice sample as an index. Specifically, the method has the following steps (a) and (b).

(a) A step of measuring a concentration of the pancreatic disease marker in a duodenal juice sample collected from a subject.

(b) A step of evaluating the possibility of suffering from pancreatic disease of the subject according to the concentration of the pancreatic disease marker measured in the step (a) and the age of the subject.

As shown in Examples which will be described later, in a pancreatic disease-unaffected subject, the concentration of the pancreatic disease marker in the duodenal juice sample tends to decrease as the age of the subject increases. Although the reason for this is not clear, it is assumed that the amount of the pancreatic juice contained in the duodenal juice decreases because the amount of the pancreatic juice discharged from the pancreatic duct decreases due to the decreased function of the pancreas.

When the cutoff value is set uniformly for all age groups according to the relationship between the concentration of the pancreatic disease marker in the duodenal juice sample and the age, the evaluation accuracy varies for each age group of the subject and the evaluation accuracy is lowered. That is, when the cutoff value is set uniformly for all age groups, in a relatively younger age group, the sensitivity is high and the specificity is low, thereby the number of false positives increases. Conversely, in a relatively elder age group, the specificity is high and the sensitivity is low, thereby the number of false negatives tends to increase.

Therefore, in order to improve the evaluation accuracy in evaluating the possibility of suffering from pancreatic disease from the concentration of the pancreatic disease marker in the duodenal juice sample so as to obtain a more reliable evaluation result, in the evaluation method according to the present invention, the possibility of suffering from pancreatic disease is evaluated according to both the concentration of the pancreatic disease marker in the duodenal juice sample and the age of the subject. The evaluation accuracy can be improved by correcting the concentration of the pancreatic disease marker in the duodenal juice sample with the age of the subject considering the natural decrease due to age with respect to the concentration of the pancreatic disease marker.

For example, the score value for the sample is calculated according to the concentration of the pancreatic disease marker in the duodenal juice sample and the age of the subject from whom the sample was sampled, and the obtained score value is compared with the cutoff value uniformly set regardless of the age of the subject, thereby, the possibility of suffering from pancreatic disease is evaluated. By making the score value from the concentration of the pancreatic disease marker considering the age of the subjects, even when compared with the uniform cutoff value for all the age groups, the variations in accuracy for each age group are suppressed and the same level of sensitivity and specificity can be achieved in every age group. The cutoff value for all age groups can be set so that the sensitivity and specificity are in a desired range, according to the ROC curve created regarding the score value of a statistically sufficient number of pancreas-diseased subjects and the score value of a statistically sufficient number of pancreatic disease-unaffected subjects.

The score value P obtained from the concentration of the pancreatic disease marker considering the age is set, for example, to a common logarithm value of the concentration of the pancreatic disease marker, compensating for the decrease due to age with respect to the concentration of the pancreatic disease marker. Specifically, for example, the score value P can be set so as to satisfy the relationship of the following equation (1).

$$\log [P/(1-P)] = a \times \log_{10}[\text{concentration of pancreatic disease marker}] + b \times [\text{age of subject}] + c \qquad (1)$$

In the equation (1), a, b, and c are real numbers determined by the multiple logistic regression analysis having an explanatory variable of the concentration of the pancreatic disease marker in the duodenal juice sample collected from a group of pancreas-diseased subjects and a group of pancreatic disease-unaffected subjects and age. The multiple logistic regression analysis can be done by a conventional method. As samples to be used by the multiple logistic regression analysis performed when the equation (1) is set, it is preferable to use the concentration of the pancreatic disease marker in the duodenal juice sample taken from a statistically sufficient number of pancreas-diseased subjects and from a statistically sufficient number of pancreatic disease-unaffected subjects respectively.

For example, in the equation (1), by setting a to 1.5 to 2.2, preferably 1.7 to 1.9, b to 0.1 to 0.2, preferably 0.12 to 0.17, and c to −20 to −15, the specificity can be adjusted to 80% or more, and preferably 90% or more in all age groups.

For example, when the pancreatic disease marker is a marker whose concentration in the duodenal juice sample collected from a pancreas-diseased subject is higher than that in the duodenal juice sample collected from a pancreatic disease-unaffected subject, a score value P is calculated from the concentration of the pancreatic disease marker in the duodenal juice sample of the subject and the age according to the equation (1), and if the obtained score value P is equal to or more than the cutoff value uniformly set regardless of the age of the subject, it is evaluated that the subject is highly likely to develop a pancreatic disease, while if the obtained score value P is less than the cutoff value, it is evaluated that the subject is less likely to develop a pancreatic disease.

In the step (b), as the cutoff value to distinguish the target group of pancreas-diseased subjects from the group of pancreatic disease-unaffected subject, the cutoff value set for each age group of the subjects can be used. The cutoff value for each age group is set to be lower as the age is elder. Each age group for which the cutoff value is set separately may be set to have an equal certain age range or may be set to have an uneven age range. For example, the age group can be set so that all ages from 0 year old are divided into age groups each having an age range of 5 years old or every 10 years old, or an age group aged under 50 years old and an age group aged equal to or over 70 years old are summarized and an age group aged 50 to 69 years old are divided into age groups having an equal certain age range.

For example, when the pancreatic disease marker is a marker whose concentration in the duodenal juice sample collected from a pancreas-diseased subject is higher than the concentration in the duodenal juice sample collected from a pancreatic disease-unaffected subject, it is evaluated that there is a high possibility that the subject is developing pancreatic disease if the concentration of the pancreatic disease marker is equal to or higher than the cutoff value set in advance for each age group, and it is evaluated that there is a low possibility that the subject is developing a pancreatic disease if the concentration of the pancreatic disease marker is lower than the cutoff value set for each age group.

The pancreatic disease marker as an indicator in the evaluation method according to the present invention is a biological molecule that has a significantly higher concentration in the pancreatic juice in a pancreas-diseased subject than in a pancreatic disease-unaffected subject and is not particularly limited. In the present invention, the pancreatic disease marker is preferably a biomolecule such as a glycoprotein or an enzyme which is hardly affected by digestive enzymes contained in the duodenal juice. The pancreatic disease marker as an indicator in the evaluation method according to the present invention is S100 calcium binding protein P (S100P), NGAL, MIC-1, CEA, CA 19-9 (for example, see Pancreas, 1994, vol. 9, No. 6, p. 741-747), MUC-1 (KL-6) (for example, see Japanese Unexamined Patent Application, First Publication No. 2006-308576), MMP 2 (Matrix Metalloproteinase-2) (for example, see Pancreas, 2002, vol. 24, No. 54, p. 344-347), MMP 7 (Matrix Metalloproteinase-7), and the like. Among them, a substance having a significantly higher concentration in the pancreatic juice of a subject suffering from pancreatic disease intended for evaluation than in a pancreatic disease-unaffected subject is preferable, such as S100P, NGAL, MIC-1, CEA and the like, and STOOP is particularly preferred. For example, since S100P secretes more from pancreatic cancer cells, using S100P as the pancreatic disease marker makes it possible to evaluate the morbidity of pancreatic cancer, which is difficult to be detected early and has a very poor prognosis, with high reliability, and thus contribute to the early detection of pancreatic cancer.

In the step (a), the duodenal juice sample to be used in the evaluation method according to the present invention may be the duodenal juice itself collected from a subject, and various additives, buffers and the like may be added to the collected duodenal juice. Examples of the additives are reagents for suppressing decomposition or denaturation of components in the duodenal juice sample such as a surfactant, a protease inhibitor, a nucleolytic enzyme inhibitor, a pH adjuster, and the like. As the buffer, a buffer used for preparation of a reaction solution for detection of proteins and nucleic acids such as phosphate physiological saline (PBS), HEPES buffer and the like can be used. Additives and the like may be added to a container containing duodenal juice collected from a living body or may be placed in a container in advance and the duodenal juice may be directly collected in the container.

The duodenal juice can be collected from a subject by a conventional method. For example, the duodenal juice can be collected by a suction means such as a syringe or a vacuum pump connected to an endoscopic catheter. Specifically, an endoscope is inserted from the oral cavity to the duodenum, and using a catheter inserted through the forceps channel, the duodenal juice existing in the second and third portions of the duodenum is aspirated and collected. For example, the duodenal juice stored in the duodenum duct may be collected while an endoscopic examination (upper endoscopic examination) of the stomach/duodenum is performed as a so-called gastro camera.

The duodenal juice sample to be used in the step (a) may be the one immediately after being taken from the subject, may be the one after being stored at room temperature, refrigerated or frozen, or may be a frozen powder obtained by freeze-drying treatment. In addition, the duodenal juice sample may be subjected to the step (a) after separating and removing the solid matter such as cells by a centrifugation treatment or the like.

In the step (a), the method of measuring the concentration of the pancreatic disease marker in the duodenal juice sample is not particularly limited as long as it is a measurement method capable of quantitatively or semi-quantitatively detecting the pancreatic disease marker in the sample. For example, by various protein analyses using ELISA, immunochromatography, two-dimensional electrophoresis, Western blotting, mass spectrometry and the like, various nucleic acid analyzes using PCR, RT-PCR, hybridization using a probe, or the like, various pancreatic disease markers can be quantitatively or semiquantitatively detected. Further, by using various analyzers such as a biochemical automatic analyzer, quantitative or semi-quantitative detection of the pancreatic disease marker can be quickly and easily performed on a large number of duodenal juice samples. These methods can be performed by a conventional method.

EXAMPLE

Next, the present invention will be described in more detail by showing examples and the like, but the present invention is not limited to the following examples.

Example 1

Of the subjects in the two medical facilities, 71 subjects including males and females whose S100P concentration is above the detection limit (>0), equal to or over 50 years old, and not having pancreatic disease or whose pancreatic cancer stage are 0, I, or IIA were statistically analyzed as for the S100P concentration in the duodenal juice samples and the presence or absence of pancreatic cancer. In subjects under 50 years old, the probability of suffering from pancreatic cancer is very low, so they were excluded from this experiment. There were 296 subjects whose STOOP concentration is above the detection limit (>0), among which, 254 subjects were equal to or over 50 years old and 42 subjects were under 50 years old.

These subjects were divided into a group of subjects not having a disease in the pancreas nor a family history of pancreatic cancer (group 1a), a group of subjects not having a disease in the pancreas but having a family history of pancreatic cancer (group 1b), a group of subjects whose pancreatic cancer stage is an early stage (stage 0 or I) (group 0/I), and a group of subjects whose pancreatic cancer stage is IIA (group IIA).

The STOOP concentration (pg/mL) in the duodenal juice sample collected from each subject was measured using a CircuLex S100P ELISA Kit (Cyclex Corporation, catalog number: CY-8060). In order to obtain the cutoff value to distinguish the group of subjects not suffering from pancreatic cancer (total of group 1a and group 1b; group 1a+1b) from the group of subjects suffering from pancreatic cancer (total of group 0/I and group IIA; group 0/I+IIA) from the measured value of S100P concentration, the ROC curve was created from the S100P concentration of each subject, and it was found that the area under the ROC curve (AUC) remained at 0.7037 (95% confidence interval: 0.5787 to 0.8038) (FIG. 1).

Figure 2:
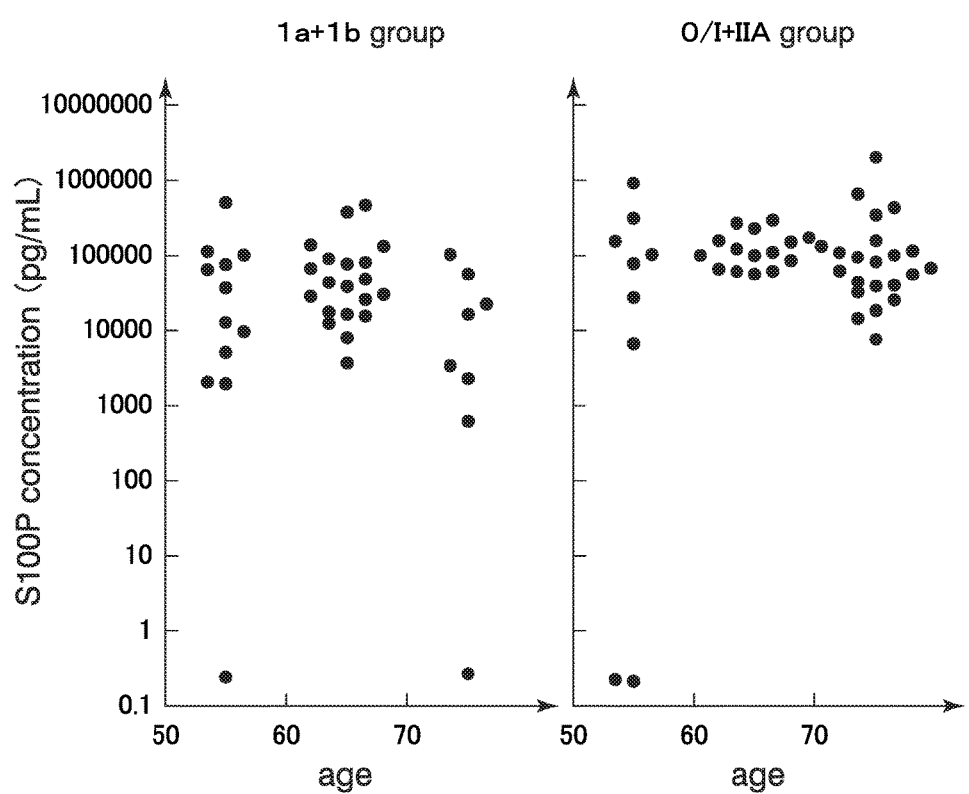
FIG. 2 is a diagram showing the plotting results of measured values of S100P concentration for each age of subjects for group 1a+1b (left figure) and group 0/I+IIA (right picture) in Example 1.

The results of plotting of measured values of S100P concentration for each age of subjects for the group 1a+1b and the group 0/I+IIA are shown in FIG. 2. As a result, in the group 1a+1b whose pancreas was normal, it was observed that the S100P concentration tended to decrease as the age increased.

Therefore, among the common logarithmic value of the S100P concentration (pg/mL) ($\log_{10}$ [pancreatic disease marker concentration (pg/mL)]), age, sex, facility, presence or absence of diabetes, presence or absence of esophageal disease, and smoking history, each of them was used as an explanatory variable of the logistic model and the relationship with the pancreatic cancer stage (group 1a+1b or group 0/I+IIA) was examined. Table 1 shows the odds ratio, 95% confidence interval, and p value in each explanatory variable. In the table, "$\log_{10}$ (S100P)" indicates the common logarithm value of the S100P concentration. As a result, the pancreatic cancer stage showed a statistically significant association with log conversion value of S100P, age, and presence or absence of diabetes, but there was no statistically significant association with sex, facility, presence or absence of esophageal disease, and smoking history.

TABLE 1

| explanatory variable | odds ratio | confidence interval | P |
|---|---|---|---|
| $\text{Log}_{10}$ (SP100P) | 3.84 | 1.46-10.13 | 0.007 |
| age | 1.10 | 1.026-1.18 | 0.007 |
| facility | 1.06 | 0.83-1.35 | 0.66 |
| presence of diabetes mellitus | 13.58 | 1.53-120.70 | 0.02 |
| presence of gullet disease | 1.10 | 0.96-1.26 | 0.18 |
| smoking history | 0.60 | 0.21-1.68 | 0.33 |

<Score Value>

In particular, since the association between common logarithm of S100P concentration and age was strong and diabetes is related to age, it was thought that there was a possibility that the association of pancreatic cancer stage and diabetes was age-related. Therefore, focusing on age, multiple logistic regression with explanatory variables of the common logarithm value of STOOP concentration and the age was performed, and a score value P1 represented by the following equation (2) was obtained.

$$\log [P1/(1-P1)] = 1.82272 \times [\text{common logarithm of } S100P \text{ concentration (pg/mL)}] + 0.13753 \times [\text{age of subject (years)}] - 18.2273 \quad (2)$$

Figure 3:
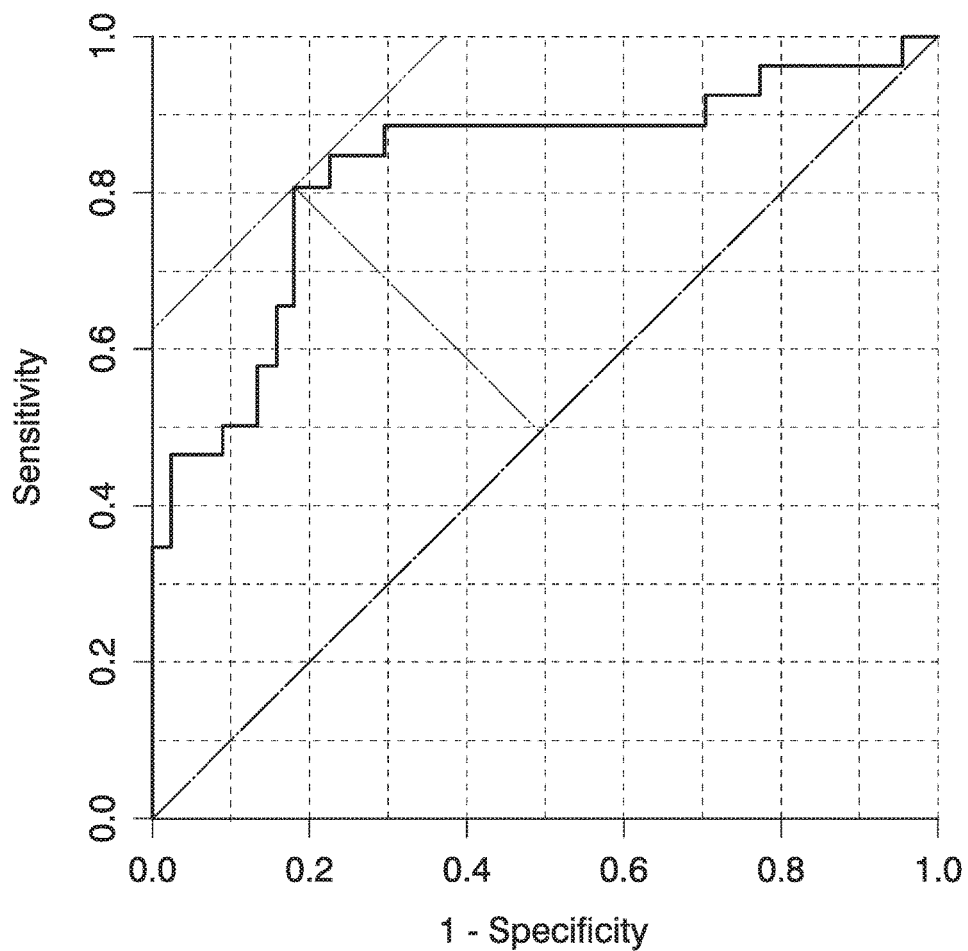
FIG. 3 is an ROC curve created from score values obtained by combining common logarithmic values of S100P concentration of each subject with the age in Example 1.

The ROC curve was created using the obtained score value P1, and the AUC increased to 0.8243 (95% confidence interval: 0.7197 to 0.9082) (FIG. 3). In order to evaluate the presence or absence of pancreatic cancer at a specificity of 90%, the score value was 0.634974, and the sensitivity in this case was 51.85%.

Next, all combinations of common logarithm values of S100P concentration, age and one or more of each of the above-mentioned three variables (facility, diabetes mellitus, esophagus disease) were added to the logistic model. The ROC curve was created from the score values obtained by each combination, and the AUC was obtained. Table 2 shows the results of detecting the difference between the AUC obtained from the logistic regression model with the above three variables and the AUC with two variables of the common logarithmic value of S100P concentration and the age. As a result, none of the cases showed a statistically significant increase from the AUC of the ROC curve obtained from the logistic model according to the two variables of the common logarithmic value of S100P concentration and the age, and it was found that the presence or absence of pancreatic cancer morbidity can be evaluated with high accuracy by the combination of the common logarithm value of the S1 OOP concentration and the age.

TABLE 2

| explanatory variable | AUC | SE | P |
|---|---|---|---|
| $\text{Log}_{10}$ (SP100P), age | 0.824 | 0.056 | |
| $\text{Log}_{10}$ (SP100P), age, facility | 0.827 | 0.054 | 0.87 |
| $\text{Log}_{10}$ (SP100P), age, presence of diabetes mellitus | 0.824 | 0.057 | 0.66 |
| $\text{Log}_{10}$ (SP100P), age, presence of gullet disease | 0.822 | 0.057 | 0.75 |
| $\text{Log}_{10}$ (SP100P), age, facility, presence of diabetes mellitus | 0.834 | 0.056 | 0.56 |
| $\text{Log}_{10}$ (SP100P), age, presence of diabetes mellitus, presence of gullet disease | 0.836 | 0.054 | 0.58 |
| $\text{Log}_{10}$ (SP100P), age, facility, presence of diabetes mellitus, presence of gullet disease | 0.820 | 0.058 | 0.86 |

<Setting of Cutoff Value for Each Age Group>

The above-mentioned 71 subjects were divided into an age group of 50 to 59 years old, a group of 60 to 69 years old and a group of equal to or over 70 years old, the ROC curve was created from the S100P concentration for each age group, and the cutoff value was determined so that the specificity was around 90%, so that the sensitivity was determined. Also, for all age groups (age group of equal to or over 50 years old), the ROC curve was created from the S100P concentration, the cutoff value was determined so that the specificity was around 90%, and the sensitivity was determined. Furthermore, for the age group of 50 to 59 years old, the age group of 60 to 69 years old, and the age group of equal to or over 70 years old, the sensitivity and specificity were calculated when the cutoff value was set as the cutoff value obtained for all age groups (uniform cutoff value). The results are shown in Table 3. In the table, "50-59" indicates the age group of 50 to 59 years old, "60-69" indicates the age group of 60 to 69 years old, "70-" indicates the age group of equal to or over 70 years old, and "50-" indicates the age group of equal to or over 50 years old.

TABLE 3

| age group | cutoff value set in each age group | | flat cutoff value (137116 pg/mL) |
|---|---|---|---|
| | cutoff value (pg/mL) | sensitivity/specificity | sensitivity/specificity |
| 50-59 | 151895 | 33.3%/91.7% | 33.3%/91.7% |
| 60-69 | 148740 | 40.0%/90.0% | 40.0%/85.0% |
| 70- | 61381 | 59.1%/87.5% | 27.3%/100% |
| 50- | 137116 | | 30.4%/90.0% |

The sensitivity and specificity when a uniformly determined cutoff value (137116 pg/mL) is used as the cutoff value are compared with the sensitivity and specificity when the cutoff value is determined so that the specificity is around 90% for each age group, and it was found that there was no particular difference in the age group of 50 to 59 years old but higher examination performance was obtained by setting the cutoff value for each age group in the age group of equal to or over 60 years old. In the age group of 60 to 69 years old, high specificity was obtained by setting the cutoff value for each age group. In the age group of equal to or over 70 years old, the specificity was increased and the sensitivity was drastically reduced with the uniform cutoff value, but both sensitivity and specificity were good with the cutoff value determined for each age group.

The age group of 60 to 69 years old was divided into the age group of 60 to 64 years old and the age group of 65 to 69 years old, the ROC curve was created from the S100P concentration for each age group, the cutoff value was determined so that the specificity was around 90%, and the sensitivity was obtained. The results are shown in Table 4. In the table, "60-64" represents the age group of 60 to 64 years old, "65-69" represents the age group of 65 to 69 years old, and "70-" represents the age group of equal to or over 70 years old. As a result, similarly to the age group of 50 to 59 years old, in the age group of 60 to 64 years old, there was not a particularly difference between the case when the uniform cutoff values were used and the case when the cutoff value was set for each age group, but in the age group of 65 to 69 years old, higher specificity was obtained in the case when the cutoff value was set for each age group than in the case when the uniform cutoff values were used.

TABLE 4

| age group | cutoff value set in each age group | | flat cutoff value (137116 pg/mL) |
|---|---|---|---|
| | cutoff value (pg/mL) | sensitivity/specificity | sensitivity/specificity |
| 50-59 | 137116 | 29.7%/89.3% | 29.7%/89.3% |
| 60-69 | 107010 | 38.7%/93.8% | 25.8%/93.8% |
| 70- | 61381 | 59.1%/87.5% | 27.3%/100% |

What is claimed is:
1. A method comprising:
(a) measuring a concentration of S100P protein in a duodenal juice sample collected from a subject suspected of suffering from pancreatic cancer; and
(b) evaluating the subject's possibility of suffering from pancreatic cancer by setting a score value from a value of the concentration of S100P protein, compensating for a decrease due to age with respect to the concentration of S100P protein, and comparing the score value with a cutoff value;
(c) determining the subject has a score value equal to or higher than the cutoff value; and
(d) administering a pancreatic cancer treatment to the subject,
wherein the concentration of S100P protein measured in the step (a) and the score value satisfy the relationship of the following equation (1):

$$\log[P/(1-P)] = a \times \log_{10}[\text{concentration of } S100P] + b \times [\text{age of subject}] + c \quad (1)$$

wherein in the equation (1):
a is in a range of 1.5 to 2.2,
b is in a range of 0.1 to 0.2,
c is in a range of −20 to −15, and
P indicates the score value.

* * * * *